United States Patent [19]

Kantrowitz et al.

[11] Patent Number: 4,630,597
[45] Date of Patent: Dec. 23, 1986

[54] DYNAMIC AORTIC PATCH FOR THORACIC OR ABDOMINAL IMPLANTATION

[76] Inventors: Adrian Kantrowitz, 70 Gallogly Rd., Pontiac, Mich. 48055; Paul S. Freed, 1486 Sodon Ct., Bloomfield, Mich. 48013

[21] Appl. No.: 604,944

[22] Filed: Apr. 30, 1984

[51] Int. Cl.⁴ .......................... A61F 1/24; A61M 1/03
[52] U.S. Cl. .................................. 128/1 D; 417/384; 623/3
[58] Field of Search ............ 128/1 D, DIG. 3; 3/1.7; 417/384; 623/3

[56] References Cited

U.S. PATENT DOCUMENTS

| | | | |
|---|---|---|---|
| 3,766,567 | 10/1973 | Kahn et al. | 3/1.7 |
| 3,974,825 | 8/1976 | Normann | 3/1.7 |
| 4,034,742 | 7/1977 | Thoma | 128/1 D |
| 4,051,840 | 10/1977 | Kantrowitz et al. | 128/1 D |
| 4,144,595 | 3/1979 | Unger | 128/1 D |
| 4,195,623 | 4/1980 | Zeff et al. | 3/1.7 |
| 4,222,127 | 9/1980 | Donachy et al. | 128/1 D |
| 4,245,622 | 1/1981 | Hutchins, VI | 3/1.7 |

FOREIGN PATENT DOCUMENTS

| | | | |
|---|---|---|---|
| 2056830 | 5/1972 | Fed. Rep. of Germany | 128/1 D |
| 545358 | 12/1977 | U.S.S.R. | 128/1 D |

*Primary Examiner*—C. Fred Rosenbaum
*Assistant Examiner*—Gene B. Kartchner
*Attorney, Agent, or Firm*—Basile, Weintraub & Hanlon

[57] ABSTRACT

An improved dynamic aortic patch is constructed with an elongate semi-rigid shell member having a concave inner surface and a flexible membrane integrally bonded to the outer surface of the shell to define an inflatable and deflatable chamber between the concave inner surface and the membrane. The pumping capacity of the patch is determined by the concavity of the inner surface of the shell member, thus enabling the construction of a patch which may be implanted in the thoracic cavity (small concavity) or in the abdomen (large concavity). A fabric layer bonded to the membrane over the area overlying the outer surface of the shell has a peripheral suture flange projecting freely clear of the membrane, and a temporary shield adapted to overlie the fabric layer may be employed to assure that sutures placed to attach the patch within an opening in the aorta are not inadvertently passed through the membrane.

3 Claims, 7 Drawing Figures

DYNAMIC AORTIC PATCH FOR THORACIC OR ABDOMINAL IMPLANTATION

BACKGROUND OF THE INVENTION

The invention described herein was made in the course of work under a grant or award from the Department of Health, Education and Welfare.

A dynamic aortic patch is a device which is permanently surgically implanted in the wall of the aorta to augment the pumping action of the heart. It is sometimes referred to as a mechanical auxiliary ventricle (MAV) or described as a permanently implanted balloon pump.

The device includes a flexible bladder which is inflated and deflated in synchronism with diastole and systole to elevate aortic blood pressure immediately after aortic valve closure. Inflation and deflation of the bladder is accomplished by means of a supply tube connected to the bladder and to a percutaneous access device which is likewise permanently surgically implanted in a patient's body to provide a through-the-skin coupling for connecting the supply tube to an extra-corporeal fluid pressure source. Electrical leads from electrodes implanted in the myocardium are likewise brought out through the skin via a percutaneous access device and the "R" wave of the electrocardiograph is employed to control the fluid pressure source in inflating and deflating the bladder in synchronism with the heart action.

The dynamic aortic patch, as noted above, acts to assist or augment the function of the left ventricle and is best described as an in-series system, as opposed to parallel systems which are capable of taking over the entire function of the left ventricle. While the dynamic aortic patch is restricted in use to patients who have some functioning myocardium, parallel systems require the use of valves. This in turn requires that such parallel systems be operated continuously, because blood clotting can occur if the system is shut down. The dynamic aortic patch, on the other hand, need not be operated full time and in fact is usually operated periodically on a scheduled on-time, off-time regimen. Because the dynamic aortic patch does not require continuous operation, the patient can be at least temporarily independent of the device for periods of one to four hours or more.

The present invention is especially directed to improvements over prior art dynamic aortic patches, an example of which is shown in U.S. Pat. No. 4,051,840. The patch of U.S. Pat. No. 4,051,840 is made up of a generally cigar-shaped external envelope which is permanently sutured in position in an inclusion in the thoracic aorta with one side of the outer envelope exposed at the exterior of the aorta and the other side forming a portion of the interior wall of the aorta. An inflatable bladder is inserted into the interior of this outer envelope after is it sutured in place, and inflation and deflation of the bladder causes the appropriate flexing of the inner wall of the outer envelope in the interior of the aorta.

Experience with the patch of U.S. Pat. No. 4,051,840 has found that there is a slow, but unavoidable, seepage or migration of fluid in the form of plasma and cell fragments through the blood-outer envelope interface into the dead space between the outer envelope and inner bladder. The outer envelope was attached to the wall of the aorta directly, and flexing of the outer envelope during operation of the device occurred closely adjacent the line of juncture between the envelope and aorta wall.

Further, the construction of the device of U.S. Pat. No. 4,051,840 essentially dictates a bladder of elongate tubular shape which in turn imposes practical limitations on the pumping capacity of the patch.

The present invention is directed to improvements in a dynamic aortic patch in which the dead space referred to above is eliminated and in which a more flexible selection of the location of the implanted device—i.e., in the thoracic cavity or in the abdomen—is made possible by a construction in which the pumping capacity may be varied by minor design changes.

SUMMARY OF THE INVENTION

A device according to the present invention includes an elongate bladder of which one longitudinal side is formed with a relatively thick, semi-rigid, inwardly concave wall which is integrally joined to the remaining relatively thin and flexible wall of the bladder. A Dacron velour layer is bonded to the outer side of the semi-rigid wall portion of the bladder and cut with a freely projecting peripheral edge portion which provides a suture flange for suturing the device in place within an incision in the aorta. A projecting connecting tube integrally formed on the semi-rigid wall portion provides a means for connecting the lumen of the bladder to a pneumatic supply source. The inner surface of the semi-rigid portion of the bladder is concave in shape and formed with a plurality of grooves which extend from the supply tube opening outwardly to the periphery of the semi-rigid portion to prevent entrapment of air bubbles within the bladder as it is being deflated.

Other objects and features of the invention will become apparent by reference to the following specification and to the drawings.

IN THE DRAWINGS

Figure 1:
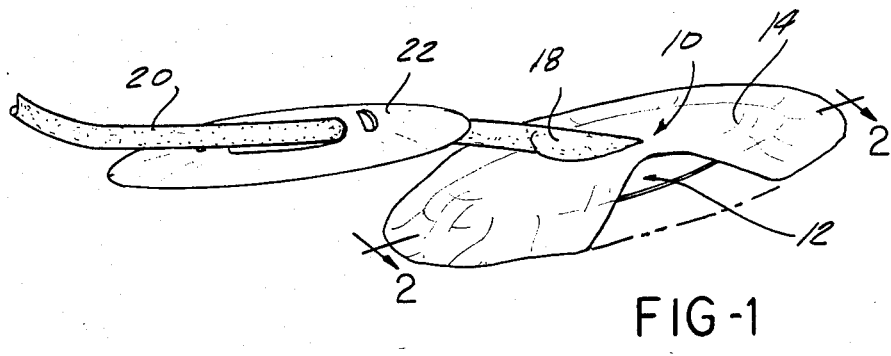
FIG. 1 is a perspective view, with certain parts broken away, of a dynamic aortic patch embodying the present invention.

Referring first to FIG. 1, a dynamic aortic patch embodying the present invention is designated generally 10 and includes a bladder designated generally 12 to one side of which is bonded a piece of Dacron velour material 14 of a type which is commercially available and which has been certified for use in implanted devices. As indicated in FIG. 1, the Dacron velour sheet 14 is cut generously to provide a peripheral hem or flange 16 which projects freely from the bladder 12 to provide a suture flange for implanting the device in an incision in the aorta as best shown in FIGS. 2 and 3.

The bladder is formed with an integral projecting tube portion 18 whose distal end is connected to one end of a supply tube 20. The patch 10 is preferably supplied with a suture template 22 in the form of a thin sheet metal shield which, during implantation, is temporarily placed upon the top of the Dacron velour layer 14. The peripheral edge of template 22 when so placed projects outwardly well beyond the periphery of bladder 12 partially across the projecting suture flange 16 so that sutures being placed will not penetrate bladder 12.

Figure 2:
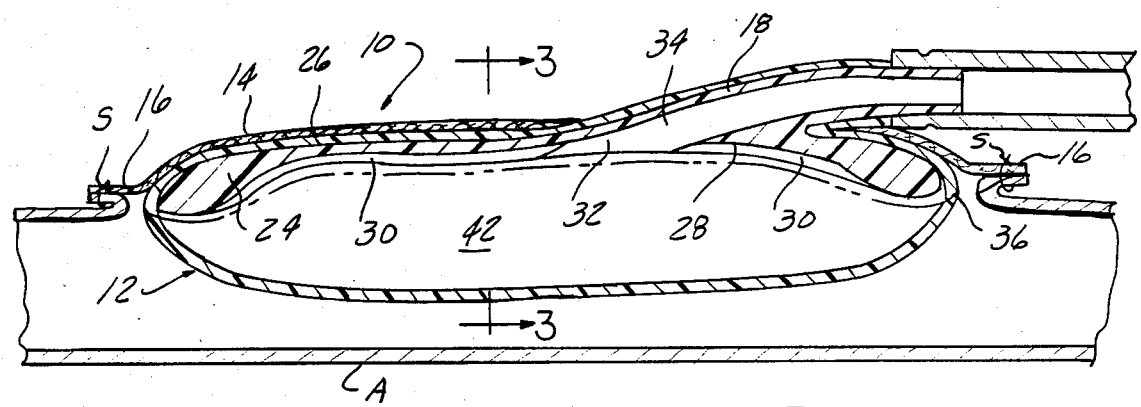
FIG. 2 is a detail cross-sectional view showing the patch of FIG. 1 implanted with the cross-sectional plane through the device lying approximately along the line 2—2 of FIG. 1.
Figure 3:
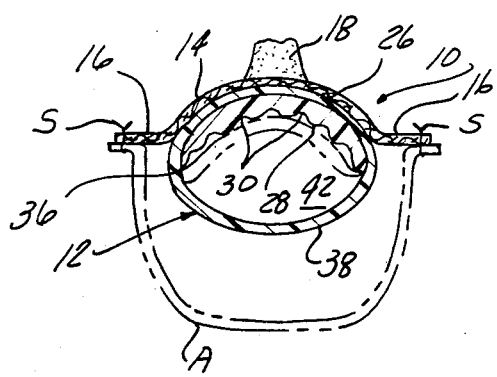
FIG. 3 is a detail cross-sectional view of the implanted device taken on the line 3—3 of FIG. 2.

Referring now particularly to FIGS. 2 and 3, the patch 10 is shown in longitudinal and transverse cross-sectional views implanted within the wall of the thoracic aorta A. To implant the device, the surgeon makes a longitudinal incision through the wall of the aorta, usually downwardly from a location just below the subclavian artery, and the device is placed within the incision in the manner shown in FIGS. 2 and 3 and sutured firmly in position by sutures S which pass through the projecting suture flange 16 of the Dacron velour web 14. The Dacron velour material has a fibrous surface into which body tissues will migrate and mechanically interweave to augment the sealing action initially established by the sutures S.

As best seen in the cross-sectional views of FIGS. 2 and 3, the outer side of bladder 12, as implanted, is a relatively thick, semi-rigid body or shell member 24 which is molded from a biocompatable urethane material, the projecting inlet tube 18 being formed integrally with the body 24. In plan, as best appreciated from FIG. 1, body 24 is of an elongate elliptical shape, while its upper or outer surface 26 is convex in both its longitudinal and transverse extents. The lower or inner surface 28 of body 24 is concave in its longitudinal extent; and in its transverse extent, as best seen in FIG. 3, surface 28 is generally concave but is provided with a plurality of grooves 30 which, as best seen in FIG. 2, extend from the opening 32 of the internal passage 34 through inlet tube 18.

The peripheral side edge 36 of body 24 is smoothly rounded throughout its entire extent.

A thin wall flexible membrane, continuous except for an opening for inlet tube 18, is then fixedly secured in face-to-face relationship with the outer side surface 26 of body 24. Membrane 38 is free from the peripheral side edges 36 and inner surface 28 of body 24. For purposes of explanation, membrane 38 and body 24 are cross hatched in FIGS. 2 and 3 as if they were separately formed.

Preferably, however, bladder 12 is formed by a known technique which results in membrane 38 and body 24 becoming what is in effect a single unitary structure.

Figure 4:
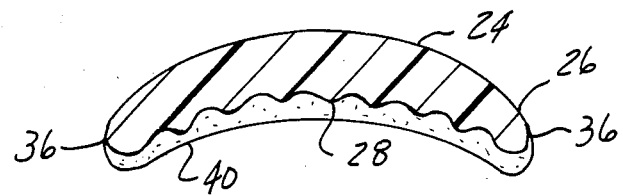
FIG. 4 is a cross-sectional view of shell member 24 at an intermediate stage of its construction.

In this particular forming technique, body 24 is molded to the form indicated in cross hatching in FIGS. 2 and 3 and is then provided with a coating of wax 40, see FIG. 4, which entirely covers the inner or lower surface 28 and the peripheral side edges 36. The wax-coated body 24 is then dipped into a commercially available Biomer lacquer to form an enclosing layer approximately 0.012 inches thick around the wax-coated body. During this process, the Biomer lacquer partially dissolves the exposed (non-wax-coated) surface of the urethane body and produces an integral structure. This particular process is known as solvation bonding. The wax 40 is subsequently melted and extracted through passage 44, thereby establishing an enclosed lumen or air chamber in the interior of bladder 12.

That portion of membrane 38 which, when implanted, would interface with blood in the aorta is then preferably flocked with Dacron fibrils and overcoated to ensure against flock release. The Dacron velour web 14 is then adhesively bonded in position and supply tube 20 is attached to the distal end of inlet tube 18 by bonding the tube in position and backing up this bond with a ligature L.

Tube 20 is led from the implanted device to an access device implanted beneath and projecting through the patient's skin, see, for example, U.S. Pat. No. 4,004,298, by means of which tube 20 (and electrocardiograph leads) may be operatively connected to or disconnected from an external pneumatic pump and controller of a known, commercially available type. In operation, as described in greater detail in the aforementioned U.S. Pat. No. 4,051,840, flexible membrane 38 is alternately flexed between the full and broken line positions of FIGS. 2 and 3 to augment the pumping action of the left ventricle.

The patch as illustrated in FIGS. 1-4 shows the bladder having what might be described as a generally cigar-shaped configuration with the semi-rigid body 24 defining roughly the upper longitudinal half of this shape.

Where the patch is to be implanted in the thoracic cavity in that position of the aorta immediately below the subclavian artery, see FIG. 6, only a relatively small volume of blood is disposed on the aorta between the patch and the left ventrical and the pumping capacity or "stroke volume" of the patch need not be very large. This is a fortunate circumstance, because the overall dimensions of a patch to be implanted at this location are restricted.

Figure 6:
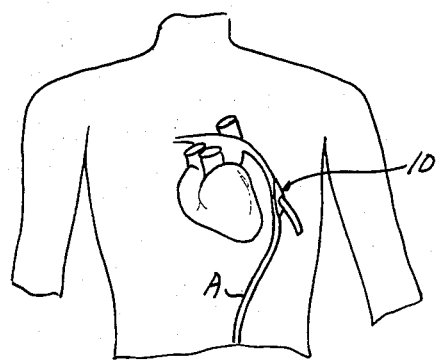
FIG. 6 is a schematic view showing the location of implantation of the patch of FIGS. 1-3.

Because thoracic surgery is a relatively high risk procedure, as compared to abdominal surgery, implantation of the patch at the location of FIG. 6 may be precluded for some patients. Implantation of prior art devices in the aorta in the abdomen has generally not been feasible because the increased distance of the device from the heart has required a relatively large capacity pump to move the blood located in the aorta between the heart and the patch. While more space is available in the abdomen, prior art devices, because they are usually by flexible construction, are subject to mechanical problems when enlarged to provide sufficient capacity for abdominal implantation.

Figure 7:
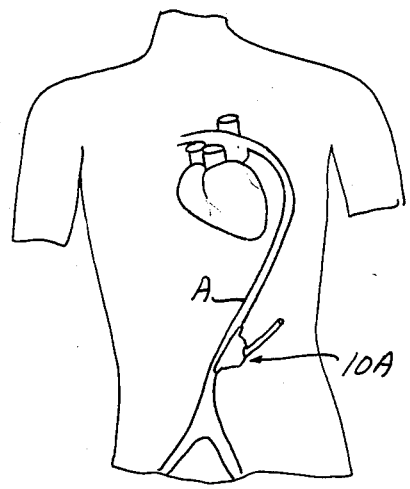
FIG. 7 is a schematic view showing an alternative location of implantation.
Figure 5:
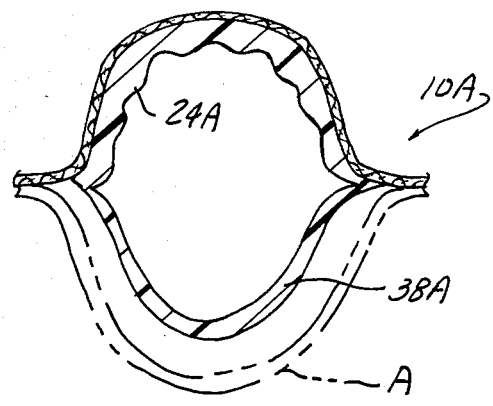
FIG. 5 is a transverse cross-sectional view, similar to FIG. 3, of a modified form of patch.

Because the patch of the present invention is formed with a semi-rigid body 24, the pumping capacity of the patch may be readily increased simply by increasing the concavity of the underside of body 24 and by modifying the shape of the body from that shown in FIGS. 1-4 to a deeper transverse cross section as shown in the device 10A of FIGS. 5 and 7. The semi-rigid body 24A provides a fixed surface against which the internal pressure within the lumen can work to expand the flexible wall 38A of the bladder. The present invention is thus particularly well adapted to be implanted below the patient's diaphragm in the abdominal cavity, thus substantially decreasing the surgical risk.

While one embodiment of the invention has been described in detail, it will be apparent to those skilled in the art that the disclosed embodiment may be modified. Therefore, the foregoing description is to be considered exemplary rather than limiting, and the true scope of the invention is that defined in the following claims.

What is claimed is:

1. In a dynamic aortic patch or the like adapted to be positioned in a aorta including a flexible bladder means in contact with blood passing through the aorta, the bladder means adapted to be cyclically inflated and deflated and conduit means for conducting fluid to and from the interior of said bladder to inflate and deflate said bladder means; the improvement wherein said bladder means comprises an elongate semi-rigid shell member having an outer surface and a concave inner surface terminating at a smoothly rounded, continuously curved peripheral side edge located between the concave inner surface and the outer surface, and a flexible, air-tight membrane bonded to said shell member continuously along the outer surface of the shell membrane immediately adjacent to the entire peripheral side edge and defining an enclosed internal chamber between said membrane and said concave inner surface of said shell membrane, said membrane having a surface area substantially equal to the surface area of said inner surface whereby said membrane lies in substantially smooth, face-to-face contact with said inner surface when said bladder means is deflated, passage means extending through said shell member for placing said internal chamber in fluid communication with said conduit means.

2. The invention defined in claim 1 further comprising means defining a plurality of grooves in said inner surface extending from said opening substantially to said peripheral side edge.

3. The dynamic aortic patch of claim 1 further comprising:
means defining peripherally projecting fabric flange secured to said semi-rigid shell member projecting outwardly from said peripheral edge and constituting a suture flange for attaching said patch to the periphery of an opening in the wall of the aorta with said shell member bridging said opening and said membrane exposed to the interior of the aorta.

* * * * *